(12) United States Patent
Palma (10) Patent No.: US 8,535,295 B2
(45) Date of Patent: Sep. 17, 2013

(54) PROTECTIVE COVER (76) Inventor: Sandra L. Palma, Fairfax, VA (US)

(*) Notice: Subject to any disclaimer, the term of this patent is extended or adjusted under 35 U.S.C. 154(b) by 1847 days.

(21) Appl. No.: 11/185,889

(22) Filed: Jul. 21, 2005

(65) Prior Publication Data
US 2006/0074367 A1  Apr. 6, 2006

Related U.S. Application Data (63) Continuation-in-part of application No. 10/956,029, filed on Oct. 4, 2004.

(51) Int. Cl.
A61M 27/00 (2006.01)
A61F 5/00 (2006.01)
A61F 13/00 (2006.01)

(52) U.S. Cl.
USPC ............ 604/543; 602/41; 602/3; 602/43

(58) Field of Classification Search
USPC ............ 602/41, 3, 6; 604/543; 128/885–888
See application file for complete search history.

(56) References Cited

U.S. PATENT DOCUMENTS

| 4,178,924 A | * | 12/1979 | Baxter ........................ 602/3 |
| 4,986,265 A | | 1/1991 | Caponi |
| 5,016,648 A | | 5/1991 | Brown et al. |
| 5,592,953 A | | 1/1997 | Delao |
| 5,817,038 A | * | 10/1998 | Orange et al. .............. 602/3 |
| 5,924,130 A | | 7/1999 | Fragomeli |
| 6,210,352 B1 | | 4/2001 | Williams et al. |
| 6,267,115 B1 | | 7/2001 | Marshel |
| 6,276,364 B1 | | 8/2001 | Warner |
| 6,512,158 B1 | | 1/2003 | Dobos |

FOREIGN PATENT DOCUMENTS

FR  2630908  * 5/1988

* cited by examiner

Primary Examiner — Jacqueline F. Stephens
(74) Attorney, Agent, or Firm — KED & Associates, LLP (57) ABSTRACT A protective cover for a site on a patient is provided which provides an effective moisture barrier to the site. The cover includes a first, absorptive layer which absorbs and wicks away any accumulated moisture on the site to keep the site dry and contaminant free, and a second, waterproof layer which precludes penetration of moisture and other such external effects to keep both the first layer and the site dry. Cuffs formed on open end portions of the second layer direct water and other such contaminants away from potential points of entry, thereby providing a further level of protection to the first layer and the site.

45 Claims, 6 Drawing Sheets

PROTECTIVE COVER

This is a Continuation in Part of application Ser. No. 10/956,029 filed Oct. 4, 2004, the entirety of which is incorporated herein by reference.

BACKGROUND OF THE INVENTION

1. Field of the Invention

This invention relates to a protective cover.

2. Background of the Related Art

Patients who have an injury to a particular area, or site, on the body which requires a relatively long healing time and/or protection from external elements, or who have a medical condition which requires access to a port site for periodic administration of medication, often have difficulty protecting these sites from contamination or damage due to external influences. One such site may be a wound, perhaps requiring stitches or administration of topical medication under a sterile dressing to facilitate the healing process. However, exposure to external elements, such as, for example, water and detergents during bathing, is often detrimental to the healing process, even when the site is covered by a sterile dressing.

Another such site may be a port insertion site. Ports are often inserted into the body of a patient to facilitate the administration of fluid and/or drug therapy, as well as for the drawing of fluids, such as blood, from a patient. These ports may be left in place for extended periods of time so that medical personnel (and/or the patient) need only to access the port to administer fluids and/or draw samples, rather than relying on temporary methods, such as a needle and syringe, which may be uncomfortable and time consuming.

An example of one such body port is a peripheral intravenous central catheter (PICC). A PICC is a long, flexible tube that is inserted into a vein in a patient's arm and threaded up into a larger vein above the heart. Medications flowing into the PICC are mixed with and carried by the blood into the bloodstream. The PICC may be left in for extended periods of time for patients requiring repeated infusion type therapy. Although this arrangement facilitates the administration of fluid therapy when required, it also leaves the PICC exposed when not in use, leaving it vulnerable to damage and contamination. This can be particularly problematic when bathing, as the PICC may be exposed to water, detergents, and the like which may contaminate the PICC and cause infection at the entry site.

Additionally, many patients may feel self conscious with an exposed PICC. Ace bandages are sometimes wrapped and secured around the port site, but these are bulky and uncomfortable to wear, do not provide ready access to the port when required, are difficult to put on and secure with one hand, and do not provide effective protection against water and/or detergents when bathing. Stockinette-type webbing is also sometimes used, but its limited elasticity and web like structure prove uncomfortable and ill fitting, do not prevent disturbance of the PICC, and likewise do not provide any protection while bathing.

Still another such site may include a cast. While a cast is typically put in place to facilitate a proper setting and healing of a bone, and not necessarily to facilitate healing of an external wound, there are still many instances in which a cast may require protection against external effects, such as water and detergents during bathing, which can easily cause degradation of the structural integrity of the cast, cause infection to the skin beneath the cast, and ultimately affect the quality of healing.

The typical solution to the problem of protecting these sites (wounds, ports, casts, and the like) while bathing, whether the site is covered by a sterile dressing or not, is to extend a plastic bag over the site and secure the bag in place with a string, or perhaps an elastic band. However, there are numerous disadvantages associated with this type of system.

A relatively minimal external force applied to an unfitted bag secured by a string or elastic band may cause slippage or movement, thus possibly exposing the site and/or a sterile dressing covering the site, to damaging moisture and the like. Further, the integrity of the bag is unknown, thus possibly allowing water to seep into the dressing and/or the site through holes in the bag. The bag is unlikely to be sterile, allowing for contamination of the dressing and/or the site by something other than water while bathing. Further, an unfitted bag cannot provide any positive retention, and slippage/friction may cause further damage to the site. Additionally, if a site to be protected happens to be on a patient's arm, the closed end of the bag must necessarily also be fitted over the patient's hand, and the patient essentially loses the use of that hand while the bag is in place.

These types of protective measures do not provide a fast, efficient, effective moisture barrier, either to the site itself, or to a sterile dressing which may be covering the site. Moisture damage to a sterile dressing usually results in that moisture penetrating the dressing and contaminating the site it is supposed to protect. Moisture damage to the sterile dressing also requires that the dressing be changed in order to maintain a sterile environment around the site, resulting in added expense, time, and inconvenience to both the patient and the care provider.

SUMMARY OF THE INVENTION

An object of the invention is to solve at least the above problems and/or disadvantages and to provide at least the advantages described hereinafter.

A protective cover for a site on a patient according to embodiments of the invention is provided, including a first, absorptive layer which covers the site, and a second, waterproof layer which covers the first layer and precludes entry of moisture and other contaminants.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements, wherein.

DETAILED DESCRIPTION OF PREFERRED EMBODIMENTS

The invention is directed to a cover for a site on a patient which is associated with, for example, a wound or a port, either of which may or may not be covered by a sterile dressing, a cast, or any other such site which requires protection, and especially to a cover configured to provide protection from external elements to which a site may be exposed during, for example, bathing. The cover may be placed directly on the site, or may be positioned so as to provide a moisture barrier to a sterile dressing positioned over the site. For purposes of discussion, any references to the "site" to be protected may also include a sterile dressing covering such a site. Certain embodiments of the invention are in the form of a flat first layer covered by a flat second layer, each layer being configured to be sequentially positioned on a body portion of a patient and secured in place by an appropriate securing mechanism.

In one embodiment, the first layer may be a substantially rectangular layer which is wrapped around a body portion so as to cover a site, and may or may not overlap itself, depending on the patient's particular needs. In other embodiments the first layer may be of a shape suited to a particular site, and sized to cover only the site. Likewise, the second layer may be a substantially rectangular layer which is wrapped around a body portion so as to cover and protect the first layer, and thus, the site, and is sized and/or shaped based on a size and/or shape of the first layer.

The first layer may be, for example, formed of a material which absorbs any moisture which may collect on or near the site and/or the dressing and which wicks that moisture away from the surface of the first layer which contacts the site to maintain a dry, contaminant free environment in the area proximate the site. This moisture may be generated by the site due to, for example, sweating, condensation due to heat generated in the area proximate the site, seepage of a wound, and the like. The first layer is preferably disposable so as to preclude site contamination due to the first layer itself, and to further maintain a sterile environment proximate the site. The first layer may be secured in place over the site in various ways, including but not limited to securing mechanisms provided at ends of the layer, such as, for example, tape, hook and loop fasteners, ties, drawstrings, elastic elements and the like.

After positioning the first layer over the site and/or wrapping the first layer about the body portion on which the site is located, the second layer may be positioned atop the first layer so as to protect the first layer from external elements such as, for example, water and detergents to which a patient is exposed during bathing. The second layer is preferably formed of a material which repels moisture generated on the outer, external side of the cover. The second layer may be a waterproof material such as, for example, latex, vinyl, or plastic. The second layer may also be disposable so as to preclude site contamination due to the second layer itself and further maintain a sterile environment proximate the site. The second layer may be secured in place over the first layer in various ways, including but not limited to securing mechanisms provided at ends of the layer, such as, for example, adhesive tape or bands, hook and loop fasteners, ties, drawstrings, elastic elements and the like. In one embodiment of the invention, after the second layer is wrapped about the appropriate body portion and secured in place atop the first layer, ends of the second layer may be folded over so as to use gravity to further direct water, detergents, and the like away from the site.

In another embodiment of the invention, the first and second layers may each be formed as a tubular, or sack-like member having one end thereof closed, and the other end thereof open so as to fully protect a site on, for example, an extremity, such as, for example, a cast positioned on a hand and arm of a patient, or a cast positioned on a foot and leg of a patient. Similar to other embodiments, in this embodiment, the extremity may be inserted into the first layer through its open end, and then the first layer may be secured as described above. The extremity covered by the first layer may then be inserted into a second layer, and the second layer secured atop the first layer as described above. In this manner, the first and second layers serve to fully protect the site from external contamination by providing coverage to the entire site.

The invention will now be discussed referring to specific embodiments of the invention disclosed in FIGS. 1A-2F of the present application.

FIGS. 1A-1I depict an embodiment of the invention wherein a cover for a site on a patient is fitted onto the site. Although a port site on an arm of a patient may be referred to and used as an example, this is done merely for ease of discussion, and it is well understood that the invention as embodied and broadly described herein may be applied to any number and types of sites which require protection, and that a site to be covered may also include a sterile dressing positioned on the site. Likewise, although tape may be referred to and used as an example of an appropriate securing mechanism used to secure each of the layers, this is done merely for ease of discussion, and it is well understood that the invention as embodied and broadly described herein may include any number, type, and combination of securing mechanisms without departing from the spirit of the invention.

Figure 1A:
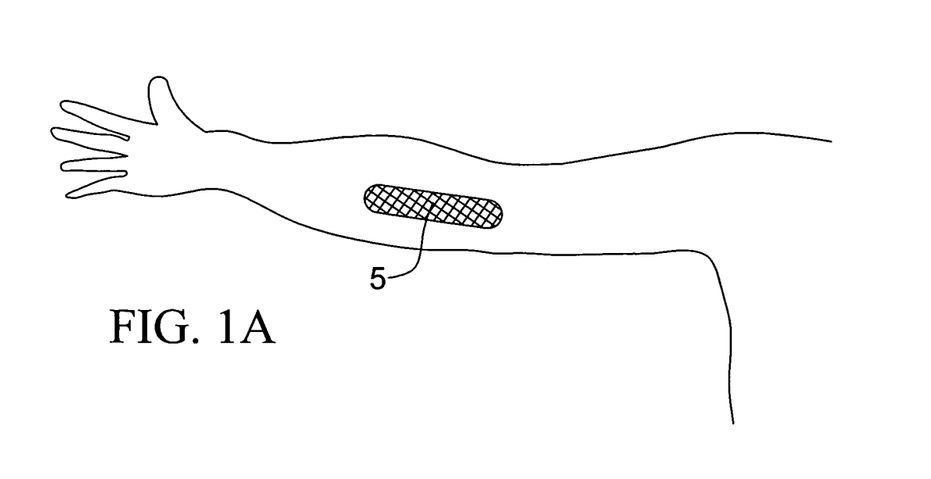
FIG. 1A shows a site on an arm of a patient which requires protection.
Figure 1B:
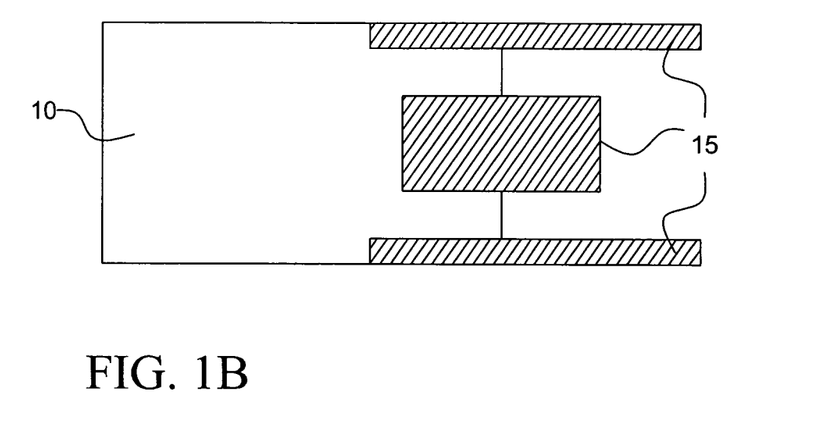
FIG. 1B is a top view of a first layer of a protective cover for the site shown in FIG. 1A, in accordance with an embodiment of the invention.
Figure 1C:
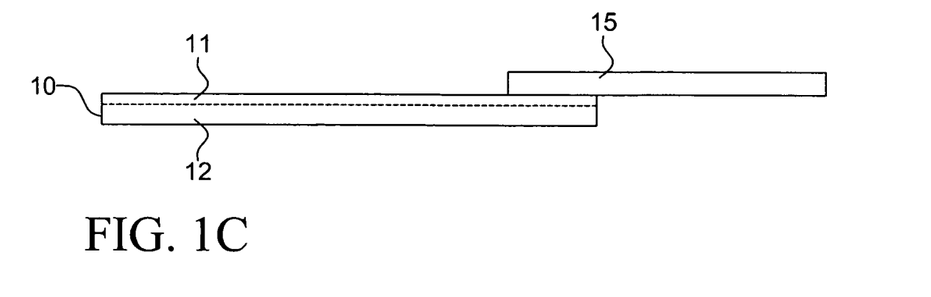
FIG. 1C is a side view of the first layer shown in FIG. 1B.

FIG. 1A shows a site 5 on an arm of a patient which requires protection from the external elements to which it is exposed while bathing. FIG. 1B is a top view of a first layer 10 configured to be fitted atop the site 5 and secured in place with a tape 15, and FIG. 1C is a side view of the first layer shown in FIG. 1B. The site 5 may or may not include a sterile dressing. In one embodiment of the invention, the first layer 10 may be made of an absorbent coated type material, with the side of the first layer 10 which contacts the site 5, or the absorbent portion 11, made of a highly absorbent paper or fabric weave to effectively absorb and wick moisture away from the site 5. A coating portion 12 may be applied to the absorbent portion 11 on the side of the first layer 10 which does not contact the site 5. The coating portion 12 may be made of a thin plastic, latex, rubber, or other such material to contain any moisture collected by the absorbent portion 11 of the first layer 10 within the first layer 10. The first layer 10 may be wrapped around the site 5 several times to provide added moisture protection and wicking to the site 5, and may be adjusted (i.e., overlapped as necessary) to properly fit around the patient's arm so as to provide a proper fit. The tape 15 is then easily secured to whatever portion of the first layer 10 necessary to secure the first layer 10 in place and provide a proper fit, as shown in FIG. 1D.

Figures 1D, 1E:
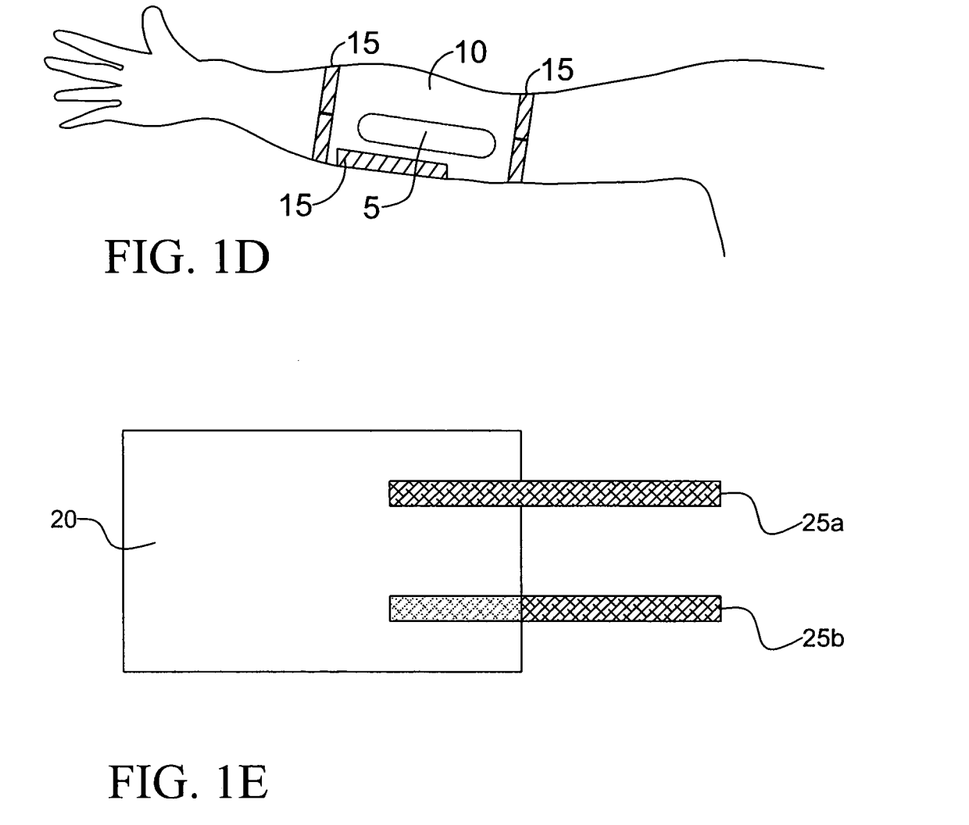
FIG. 1D shows the first layer of FIG. 1B positioned and secured on the site shown in FIG. 1A.
FIG. 1E shows a second layer of a protective cover for the site shown in FIG. 1A, in accordance with an embodiment of the invention.
Figure 1F:
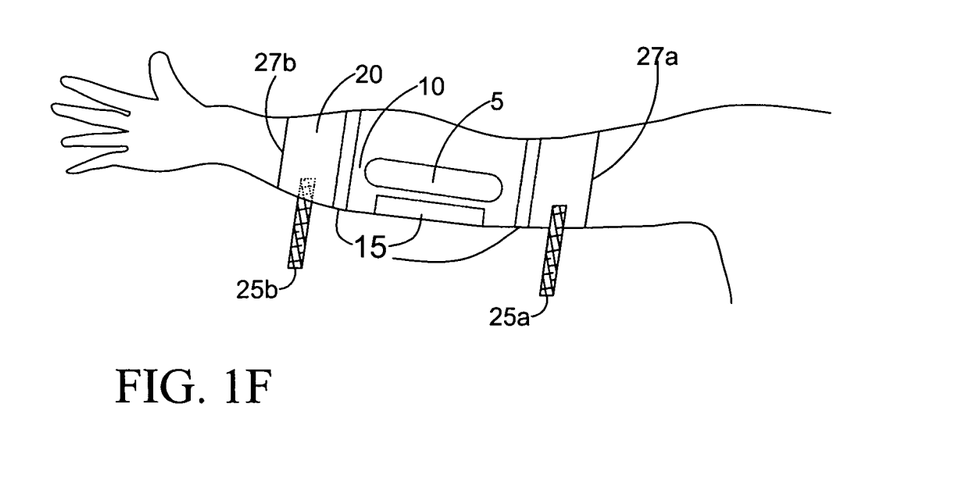
FIG. 1F shows the second layer of FIG. 1E positioned atop the first layer shown in FIG. 1D.
Figure 1G:
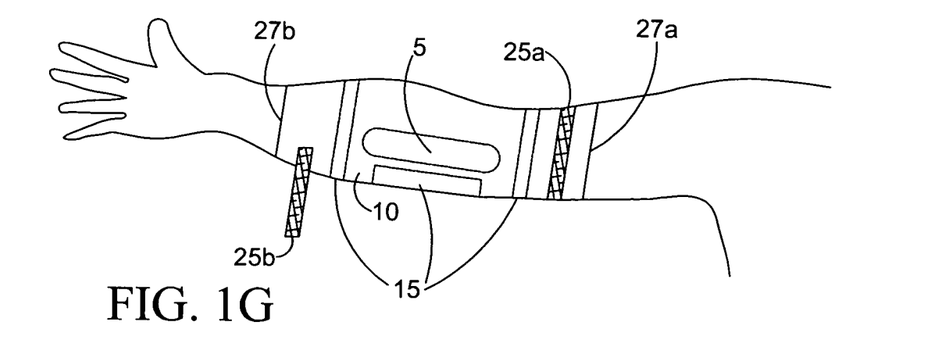
FIGS. 1G-1I show the second layer of FIGS. 1E and 1F secured atop the first layer shown in FIG. 1D.
Figure 1H:
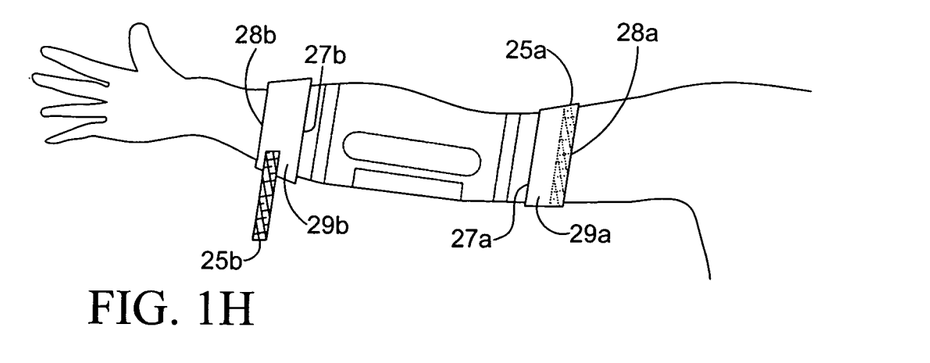
Figure 1I:
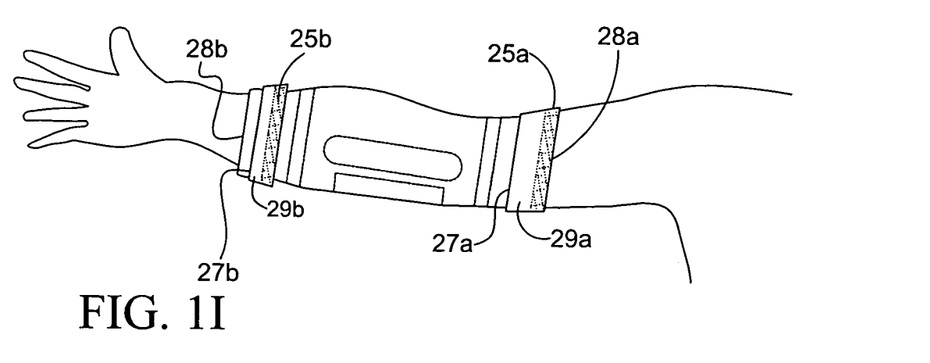

FIG. 1E shows a second layer 20 configured to be fitted atop the first layer 10, adjusted, and secured in place with tape 25. It is noted that, in this particular embodiment, a first tape 25a is provided on an outer, external side of the second layer 20 which is exposed to the elements, while a second tape 25b is provided on an inner side of the second layer 20 which contacts the first layer 10. Similar to the first layer 10, as the second layer 20 is wrapped around the site 5, the second layer 20 may be adjusted (i.e., overlapped as necessary) to properly fit around the patient's arm and the first layer 10 so as to provide a proper fit, as shown in FIG. 1F. The first tape 25a may then be easily secured to whatever portion of the second layer 20 necessary to secure that end of the second layer 20 in place and provide a proper fit, as shown in FIG. 1G. The opposite end of the second layer 20 is, at this point, not yet secured by the second tape 25b. Ends 27a and 27b of the second layer 20 may be folded over as shown in FIG. 1H to form cuffs 29a and 29b at each end of the second layer 20. The second tape 25b, which was exposed as the end 27b was folded over, may then be secured, and the end 27b folded over again to form a cuff 29b as shown in FIG. 1I. The cuffs 29a and 29b provide a more secure waterproof seal and use gravity to naturally direct the flow of water, detergents, and the like away from potential points of entry 28a and 28b to the site 5. Further, because the second layer 20 is preferably waterproof, the second layer 20 provides an effective moisture barrier to the first layer 10, and thus to the site 5.

This system for protecting the site 5 provides an effective moisture barrier for the site 5. More particularly, the first layer 10 not only absorbs moisture, but also wicks moisture away from contact with the site 5 which may collect on or near the site 5 due to, for example, sweating, steam, seepage, and the like. The waterproof second layer 20 precludes entry of water, detergents, and the like, from outside the site 5 and cover, and thus contamination of the site 5, due to such external elements. This is especially advantageous in the case of a site which requires a sterile dressing, in that it keeps the dressing dry and contaminant free, thus eliminating the need for otherwise unnecessary dressing changes.

The embodiment of the invention shown in FIGS. 2A-2F allows an extremity of a patient to be fully covered for protection of a site during an activity such as, for example, bathing. This type of cover may be useful when, for example, a site to be protected is on a hand or foot, or when a site to be protected is a cast which extends along the arm or leg and onto a hand or foot, respectively. For ease of discussion, FIGS. 2A-2F show a cast positioned on an arm and hand of a patient. However, it is well understood that the invention as embodied and broadly described herein may be applied to any number, types, and location of sites which require such protection. Similarly, the invention as embodied and broadly described herein may include any number, type, and combination of securing mechanisms without departing from the spirit of the invention.

Figure 2A:
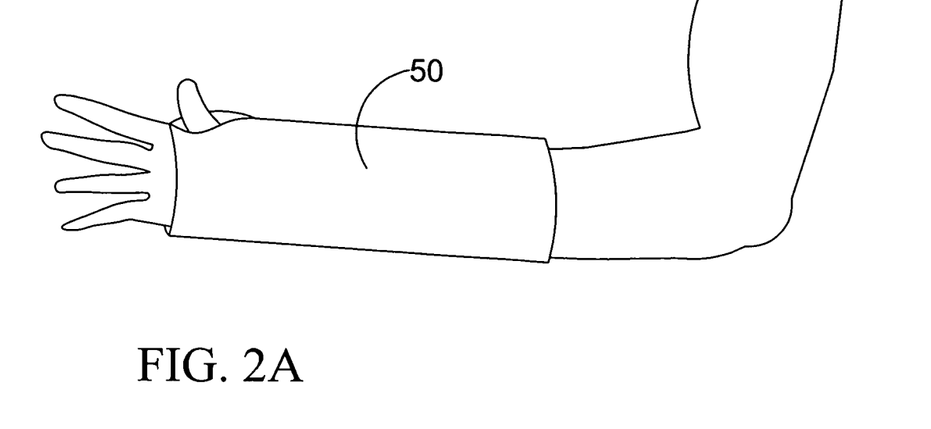
FIG. 2A shows a site on an arm of a patient which requires protection.
Figure 2B:
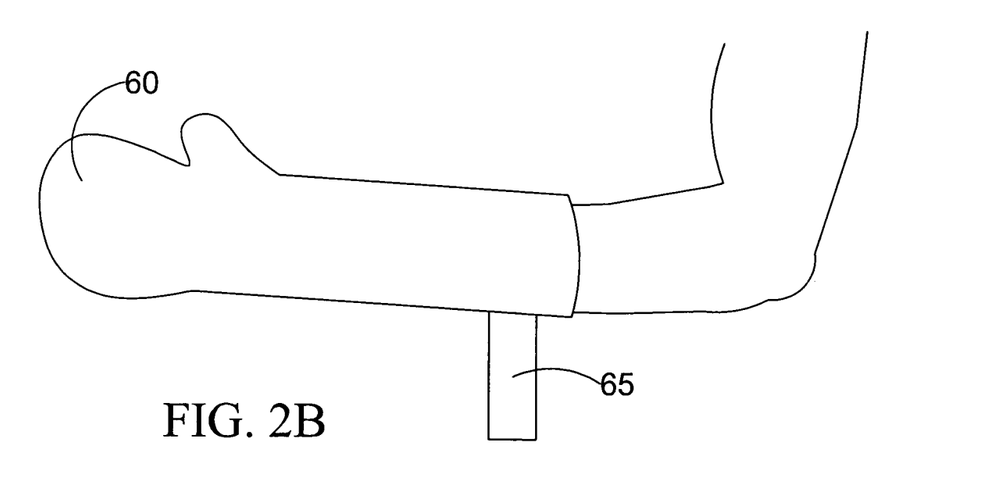
FIG. 2B is a side view of a first layer of a protective cover for the site shown in FIG. 2A, in accordance with an embodiment of the invention.
Figure 2C:
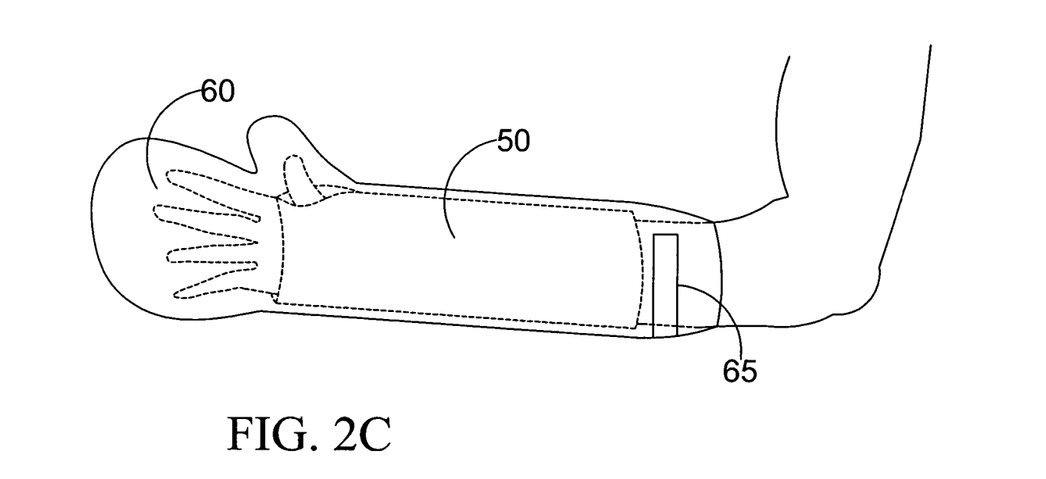
FIG. 2C shows the first layer of FIG. 2B positioned and secured on the site shown in FIG. 2A.

FIG. 2A shows a cast 50 positioned on an arm and hand of a patient, and FIG. 2B shows a first layer 60 of a cover system for the cast 50. The first layer 60 may also be merely a sheet of material configured to absorb and wick moisture away from the cast 50. That is, the material of the first layer 60 may merely be wrapped around the cast 50 any number of times and secured. The first layer 60 absorbs and wicks moisture away from the cast 50, and may be held securely in place over the cast by a securing mechanism, such as tape 65 as shown in FIG. 2C.

Figure 2D:
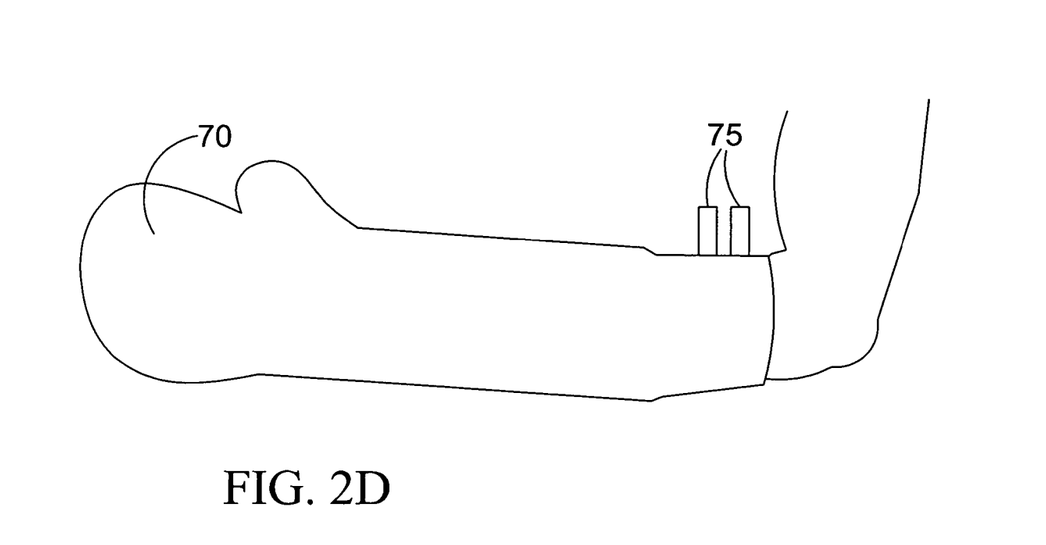
FIG. 2D is a side view of a second layer of a protective cover for the site shown in FIG. 2A, in accordance with an embodiment of the invention.
Figure 2E:
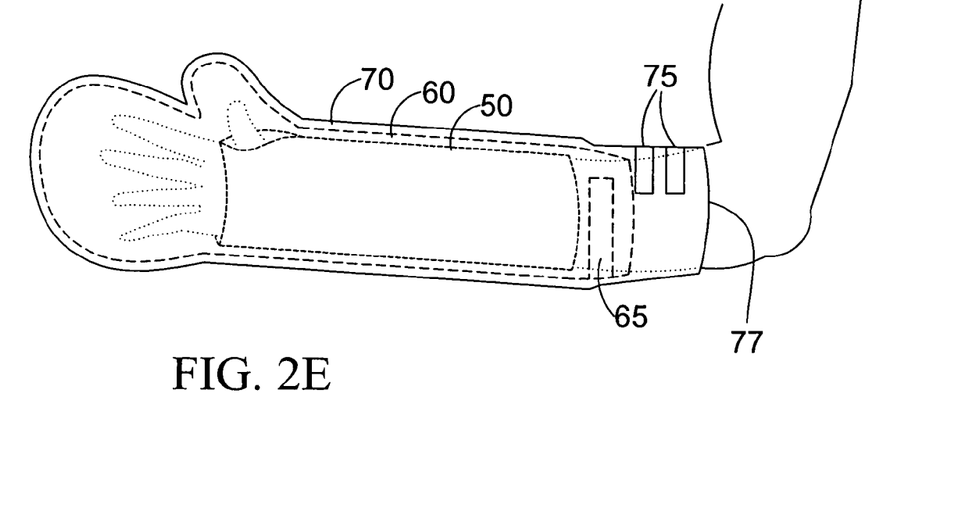
FIGS. 2E and 2F show the second layer of FIG. 2D positioned and secured on the first layer shown in FIG. 2C.
Figure 2F:
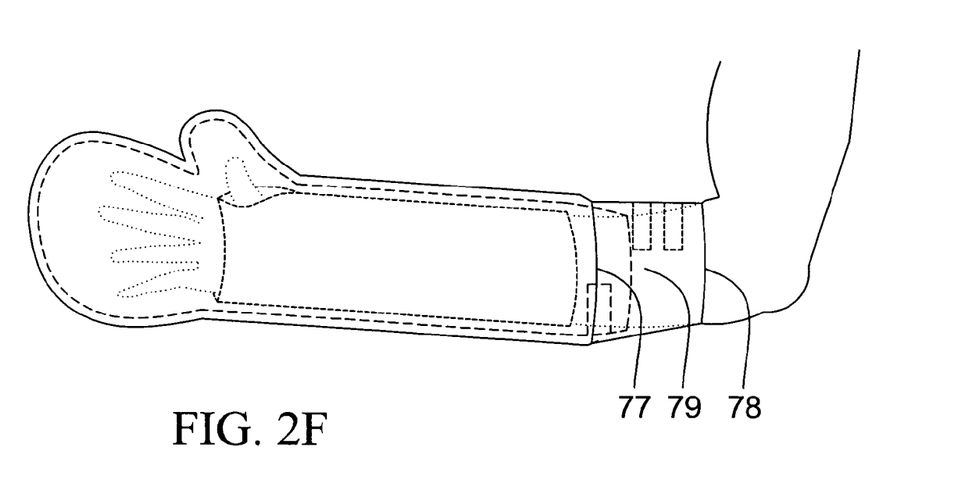

A second, preferably waterproof, layer 70 is shown in FIG. 2D. The second layer 70 may be positioned over the first layer 60 and securely held in place by tape 75, as shown in FIG. 2E. The single, open end 77 of the second layer 70 may be folded over as shown in FIG. 2F to form a cuff 79 which provides a more secure waterproof seal and directs water, detergents, and the like away from a potential point of entry 78 to the cast 50. Thus, an effective moisture barrier is provided for the cast 50, as the first layer 60 not only absorbs, but also wicks away moisture which may collect on the cast 50, while the waterproof second layer 70 precludes entry of water, detergents, and the like, and thus contamination or degradation of the cast 50 due to such external elements.

It is well understood that the protective cover according to embodiments of the invention may be positioned covering any location, or site, which must be covered during bathing or the like, including, but not limited to the arm, hand, leg, foot, torso, neck, etc. Likewise, in the examples shown in FIGS. 1-2, the cover is worn by a human. However, the cover may also be adapted to fit an animal which has a site which may require similar protection.

The foregoing embodiments and advantages are merely exemplary and are not to be construed as limiting the invention. The present teaching can be readily applied to other types of apparatuses. The description of the invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. A protective cover for a site on a patient, comprising:
   A first layer configured to completely cover the site, wherein the first layer comprises an absorptive material that extends along substantially an entire length and width of the first layer, wherein the first layer is configured to absorb moisture accumulated on the site and to wick the absorbed moisture away from the site; and
   A separate second layer configured to completely cover the first layer, wherein the second layer comprises a material configured to substantially prevent the ingress of materials and fluids;
   wherein the first layer comprises a first layer fastening mechanism configured to releasably secure the first layer in position over the site;
   wherein the first layer fastening mechanism comprises a fastener connected to and extending from a top portion of the end portion of the first layer from which it extends, and a fastener connected to and extending from a bottom portion of the end portion of the first layer from which it extends.

2. The cover of claim 1, wherein the first layer is substantially rectangular, and wherein the first layer fastening mechanism comprises at least one first layer fastener extending from an end portion of the first layer.

3. The protective cover of claim 2, wherein the first layer is configured to be wrapped repeatedly around an extremity of a patient on which the site is disposed.

4. The protective cover of claim 2, wherein a first end of the at least one first layer fastener is connected to the end portion of the first layer from which it extends, and a second end of the at least one first layer fastener is fastened to a portion of the first layer based on a positioning of the first layer on the site.

5. The protective cover of claim 2, wherein the at least one first layer fastener comprises an adhesive tape.

6. The protective cover of claim 1, wherein the second layer comprises a second layer fastening mechanism configured to releasably secure the second layer in position on the first layer.

7. The protective cover of claim 6, wherein the second layer is substantially tubular and is configured to surround an extremity of a patient on which the site is disposed.

8. The protective cover of claim 6, wherein the second layer is substantially rectangular, and wherein the second layer fastening mechanism comprises at least one fastener extending from an end portion of the second layer.

9. The cover of claim 8, wherein the second layer fastening mechanism comprises an upper fastener connected to and extending from an upper, outward facing end portion of the second layer, and a lower fastener connected to and extending from a lower, inward facing end portion of the second layer.

10. The protective cover of claim 8, wherein a first end of the at least one fastener is connected to the end portion of the second layer from which it extends, and a second end of the fastener is fastened to a portion of the second layer based on a positioning of the second layer on the first layer.

11. The protective cover of claim 8, wherein the at least one fastener comprises an adhesive tape.

12. The protective cover of claim 1, wherein the second layer comprises a cuff portion formed at each end portion of the second layer, and wherein the cuff portions are configured to direct external materials and fluids away from a corresponding point of entry under the second layer.

13. The protective cover of claim 12, wherein the external materials and fluids comprise at least one of water and detergents encountered during bathing or physical therapy.

14. The protective cover of claim 1, wherein the first and second layers are independent layers.

15. The protective cover of claim 1, wherein the first layer and second layer are configured to cover at least one of a wound, a port inserted into a patient's body, or a cast.

16. The protective cover of claim 15, wherein the cover is configured to cover a cast, wherein the first layer is substantially tubular in shape, with a first end thereof open to receive and cover the site, and a second end thereof closed so as to contain the site within the first layer.

17. The protective cover of claim 16, wherein the second layer is substantially tubular in shape, with a first end thereof open to receive and cover the site and the first layer, and a second end thereof closed so as to contain the site and the first layer within the second layer.

18. The protective cover of claim 17, wherein the open end of the first layer is secured by a first layer fastening mechanism, and the open end of the second layer is secured by a second layer fastening mechanism, and wherein a cuff is formed at the open end of the second layer so as to direct external materials and fluids away from a corresponding point of entry under the second layer.

19. The protective cover of claim 17, wherein the open ends of the first and second layers are secured by at least one fastener extending around corresponding upper and lower ends of the first and second layers.

20. The protective cover of claim 1, wherein the first layer comprises water resistant material coated on a first side of the absorptive material, wherein a second side of the absorptive material opposite the first side is configured to be positioned facing the site so as to absorb moisture accumulated on the site and to wick the absorbed moisture away from the site, and wherein the water resistant material contains moisture absorbed from the site by the absorptive material within the absorptive material, and prevents moisture from outside of the first layer from passing therethrough.

21. The protective cover of claim 1, wherein the first layer comprises a plastic coated paper material.

22. The protective cover of claim 1, wherein the second layer comprises a second layer fastening mechanism configured to releasably secure the second layer in position on the first layer.

23. The protective cover of claim 22, wherein the second layer fastening mechanism comprises elastic provided at upper and lower ends of the second layer, wherein the elastic is configured to secure the second layer to the first layer and the first and second layers in place relative to the site.

24. The protective cover of claim 22, wherein the second layer is substantially tubular and is configured to surround an extremity of a patient on which the site is disposed.

25. The protective cover of claim 24, wherein the second layer fastening mechanism comprises an upper fastener connected to and extending from an upper end portion of the second layer, and a lower fastener connected to and extending from a lower end portion of the second layer.

26. A method for protecting a site on a patient, comprising:
positioning a first layer of a protective cover over a site on a patient so as to completely cover the site, wherein the first layer comprises an absorptive material extending along substantially an entire length and width of the first layer, wherein the first layer absorbs moisture accumulated on the site and wicks the absorbed moisture away from the site;
positioning a second layer of the protective cover over the first layer so as to completely cover the first layer; and
securing the first and second layers in place on the site.

27. The method of claim 26, wherein securing the first and second layers comprises securing the first layer in place on the site using a first layer fastening mechanism after the first positioning step and before the second positioning step.

28. The method of claim 27, wherein the second positioning step comprises positioning a second layer over the first layer and wherein the second layer comprises a material which is configured to substantially prevent the ingress of materials and fluids.

29. The method of claim 27, wherein positioning a first layer of a protective cover over a site further comprises repeatedly wrapping the first layer around an extremity of a patient on which the site is disposed.

30. The method of claim 27, wherein securing the first and second layers further comprises securing the second layer on the first layer using a second layer fastening mechanism after securing the first layer and positioning the second layer.

31. The method of claim 26, wherein the first positioning step comprises positioning a first layer of a protective cover over at least one of a wound, a port inserted in a patient's body, and a cast.

32. The method of claim 26, wherein the second positioning step comprises positioning an independent second layer over the first layer.

33. The method of claim 26, further comprising forming a cuff at at least one end of the second layer so as to direct external materials and fluids away from at least one corresponding point of entry under the second layer.

34. The method of claim 33, wherein forming a cuff at at least one end of the second layer comprises:
securing an upper end of the second layer with an upper fastening mechanism;
folding the upper end of the second layer over to form a cuff at the upper end of the second layer;

folding a lower end of the second layer over to form a cuff at the lower end of the second layer;

securing the lower end of the second layer with a lower fastening mechanism; and folding the lower end of the second layer over the lower fastening mechanism to form a double cuff at the lower end of the second layer.

35. The method of claim 26, wherein securing the first and second layers comprises securing both the first and second layers on the site using a second layer fastening mechanism.

36. A kit for covering a site on a patient, comprising:

a first layer comprising an absorptive material extending along substantially an entire length and width of the first layer, wherein the first layer is configured to absorb moisture accumulated on the site and to wick the absorbed moisture away from the site;

a separate second layer configured to completely cover the first layer, the second layer comprising a material which is configured to substantially prevent ingress of materials and fluids; and a second layer fastening mechanism configured to secure the second layer in place relative to the site.

37. The kit of claim 36, further comprising a first layer fastening mechanism configured to secure the first layer atop the site, wherein the first layer is substantially rectangular, and wherein the first layer fastening mechanism comprises at least one first layer fastener extending from an end portion of the first layer.

38. The kit of claim 37, wherein the first layer is configured to be wrapped repeatedly around an extremity of the patient on which the site is disposed.

39. The kit of claim 37, wherein the second layer is substantially rectangular, and wherein the second layer fastening mechanism comprises at least one second layer fastener extending from an end portion of the second layer.

40. The kit of claim 39, wherein the second layer fastening mechanism comprises a fastener connected to and extending from an upper, outward facing end portion of the second layer, and a fastener connected to and extending from a lower, inward facing end portion of the second layer.

41. The kit of claim 36, wherein the second layer is substantially tubular and is configured to surround an extremity of the patient on which the site is disposed.

42. The kit of claim 41, wherein the second layer fastening mechanism comprises an upper fastener connected to and extending from an upper end portion of the second layer, and a lower fastener connected to and extending from a lower end portion of the second layer.

43. The kit of claim 36, wherein the second layer is configured to form a cuff portion at each end portion of the second layer, and wherein the cuff portions are configured to direct external materials and fluids away from a corresponding point of entry under the second layer.

44. The kit of claim 36, wherein the kit is configured to cover at least one of a wound, a port inserted into a patient's body, and a cast.

45. The kit of claim 36, wherein the first layer comprises a plastic coated paper material comprising absorptive layer and a water resistant layer coated on the absorptive layer, wherein the absorptive layer is configured to absorb moisture accumulated on the site and to wick the absorbed moisture away from the site, and the water resistant layer is configured to contain the moisture absorbed by the absorptive layer within the first layer.

* * * * *